(12) United States Patent
Hwa et al.

(10) Patent No.: US 8,552,029 B2
(45) Date of Patent: Oct. 8, 2013

(54) QUINOLINE DERIVATIVES AND USES OF THE SAME

(75) Inventors: Kuo-Yuan Hwa, Taipei (TW); Yu-May Lee, Taipei (TW); Yeh-Long Chen, Taipei (TW); Cherng-Chyi Tzeng, Taipei (TW); Hsin-Yuan Cho, Taipei (TW)

(73) Assignee: National Taipei University of Technology, Taipei (TW)

(*) Notice: Subject to any disclaimer, the term of this patent is extended or adjusted under 35 U.S.C. 154(b) by 0 days.

(21) Appl. No.: 13/366,697

(22) Filed: Feb. 6, 2012

(65) Prior Publication Data

US 2013/0096157 A1   Apr. 18, 2013

(30) Foreign Application Priority Data

Oct. 18, 2011   (TW) .............................. 100137676 A

(51) Int. Cl.
*A61K 31/47* (2006.01)
*A61P 35/00* (2006.01)
*C07D 215/233* (2006.01)

(52) U.S. Cl.
USPC .......................................... 514/312; 546/156

(58) Field of Classification Search
None
See application file for complete search history.

(56) References Cited

U.S. PATENT DOCUMENTS

2003/0219718 A1* 11/2003 Weber et al. ...................... 435/4

OTHER PUBLICATIONS

Richard B. Silverman, The Organic Chemistry of Drug Design and Drug Action, Chapter 2: Drug Discovery, Design, and Development, Academic Press, p. 5-51 (1992).*

"What is Cancer? What Causes Cancer?" [online]. Medical News Today, 2012 [retrieved on Jan. 18, 2013]. Retrieved from the Internet: <URL: http://www.medicalnewstoday.com/info/cancer-oncology/>.*

Yeh-Long Chen et al., "Synthesis and Antibacterial Evaluation of Certain Quinolone Derivatives", J. Med. Chem., vol. 44, 2001, Taiwan, pp. 2374-2377.

* cited by examiner

*Primary Examiner* — Janet Andres
*Assistant Examiner* — Timothy R Rozof
(74) *Attorney, Agent, or Firm* — Grossman, Tucker, Perreault & Pfleger, PLLC

(57) ABSTRACT

Provided is a quinoline derivative of Chemical Formula (I):

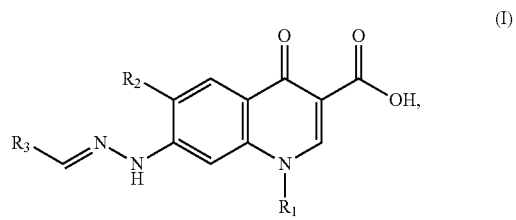

wherein, $R_1$ is a substituted or unsubstituted phenyl group, $R_2$ is a halogen, and $R_3$ is a substituted or unsubstituted phenyl group, and one of the carbon atoms in the phenyl ring of the phenyl group is optionally substituted by a nitrogen atom (N). The quinoline derivative can efficiently inhibit cancer cell proliferation and can be used for treating cancer, especially for treating cancers related to the Janus kinase-signal transducers and activators of transcription (JAK-STAT) pathway and/or the mitogen-activated protein kinase (MAPK) pathway.

12 Claims, 3 Drawing Sheets

SEQUENCE LISTING

```
<160> NUMBER OF SEQ ID NOS: 6

<210> SEQ ID NO 1
<211> LENGTH: 19
<212> TYPE: DNA
<213> ORGANISM: artificial sequence
<220> FEATURE:
<223> OTHER INFORMATION: sense primer for GADD153 gene in RT-PCR

<400> SEQUENCE: 1
gggaagtaga ggcgactcg                                                 19

<210> SEQ ID NO 2
<211> LENGTH: 18
<212> TYPE: DNA
<213> ORGANISM: artificial sequence
<220> FEATURE:
<223> OTHER INFORMATION: antisense primer for GADD153 gene in RT-PCR

<400> SEQUENCE: 2
```

```
cttcccctg cgtatgtg                                                    18

<210> SEQ ID NO 3
<211> LENGTH: 22
<212> TYPE: DNA
<213> ORGANISM: artificial sequence
<220> FEATURE:
<223> OTHER INFORMATION: sense primer for CASP3 gene in RT-PCR

<400> SEQUENCE: 3
agaactggac tgtggcattg ag                                              22

<210> SEQ ID NO 4
<211> LENGTH: 22
<212> TYPE: DNA
<213> ORGANISM: artificial sequence
<220> FEATURE:
<223> OTHER INFORMATION: antisense primer for CASP3 gene in RT-PCR

<400> SEQUENCE: 4
gcttgtcggc atactgtttc ag                                              22

<210> SEQ ID NO 5
<211> LENGTH: 21
<212> TYPE: DNA
<213> ORGANISM: artificial sequence
<220> FEATURE:
<223> OTHER INFORMATION: sene primer for actin gene in RT-PCR

<400> SEQUENCE: 5
gctcgtcgtc gacaacggct c                                               21

<210> SEQ ID NO 6
<211> LENGTH: 25
<212> TYPE: DNA
<213> ORGANISM: artificial sequence
<220> FEATURE:
<223> OTHER INFORMATION: anti-sense primer for actin gene in RT-PCR

<400> SEQUENCE: 6
caaacatgat ctgggtcatc ttctc                                           25
```

QUINOLINE DERIVATIVES AND USES OF THE SAME

This application claims priority to Taiwan Patent Application No. 100137676 filed on Oct. 18, 2011.

CROSS-REFERENCES TO RELATED APPLICATIONS

Not applicable.

BACKGROUND OF THE INVENTION

1. Field of the Invention

The present invention relates to quinoline derivatives and use of the same, especially to quinoline derivatives for treating cancers and use of the same.

2. Descriptions of the Related Art

Cancers can happen to people at any age, and in any organ or tissue of human body, causing the death of about six million people worldwide per year. Every kind of cancer begins with abnormal and uncontrollable cell division and growth, in which neoplastic cells form into malignant tumors. Tumors invade nearby tissues, transfer to regional lymph nodes through the blood or lymphatic system, and spread to more distant parts of the body through the metastatic process. Until now, the exact causes of a cancer in a human subject are not clear; however, many factors including genetics, chromosome breakage, virus, environmental factors, immune diseases, and so on are known to be relevant to the growth or metastasis of tumor cells.

Generally, the developed treatments for cancers include surgery, radiation therapy, chemotherapy, and other methods. The removal of cancerous tissue through surgery is a drastic approach, which may not only cause severe consequences, but may be also unable to remove the cancer cells completely. For example, surgery for cervical cancer and bladder cancer may cause infertility or sexual dysfunction; the need to remove all or part of a pancreatic gland in surgery for pancreatic cancer causes severe damage to a patient' metabolic functions; surgery for prostatic cancer increases the risk of uroclepsia; and surgery for lung cancer needs to cut the rib to do the procedure of removing cancerous lung tissue, thus, causing severe post-operative pain.

Radiation therapy worked by high wave energy radiation beams or particle beams which are able to penetrate materials is applied onto cancerous tumors to kill cancerous cells or prevent the growth and proliferation thereof. However, healthy tissue or surrounding cells are often affected or even killed during radiation therapy, which then leads to side effects such as fatigue, hair loss, abnormality of immune system, and loss of appetite.

Many anticancer drugs have been developed (such as 5-Fluorouracil, Herceptin, Tykerb and the like) for use in chemotherapy. Therapeutic effects can be reached through the oral administration, intramuscular injection, and intravenous injection of these drugs. However, present anticancer drugs still fail to achieve a satisfying degree of specificity. When chemotherapy is carried out, usually the normal cells in the body are also killed, and thus, may greatly influence the physiological function of the body and cause many side effects.

In view of the above limitations and faults of the known cancer therapies, the development of more effective anticancer treatments or drugs is in demand. The present invention is developed for the above demand. The inventors of the present invention developed quinoline derivatives which can efficiently inhibit the proliferation of cancer cells and can be used for treating cancers.

SUMMARY OF THE INVENTION

The primary objective of this invention is to provide a quinoline derivative represented by Chemical Formula (I):

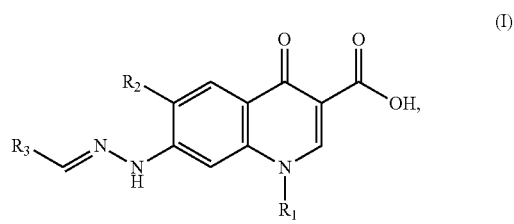

wherein,
$R_1$ is a substituted or unsubstituted phenyl group;
$R_2$ is a halogen; and
$R_3$ is a substituted or unsubstituted phenyl group, and one of the carbon atoms in the phenyl ring of the phenyl group is optionally substituted by a nitrogen atom (N).

Another objective of this invention is to provide a pharmaceutical composition, comprising a pharmaceutically acceptable carrier, and an effective amount of the quinoline derivative represented by Chemical Formula (I), or a pharmaceutically acceptable salt or ester thereof.

Yet another objective of this invention is to provide a method for treating cancers in a subject, comprising administrating to the subject an effective amount of the quinoline derivative represented by Chemical Formula (I) or a pharmaceutically acceptable salt or ester thereof.

The detailed technology and preferred embodiments implemented for the subject invention are described in the following paragraphs accompanying the appended drawings for people skilled in this field to well appreciate the features of the claimed invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
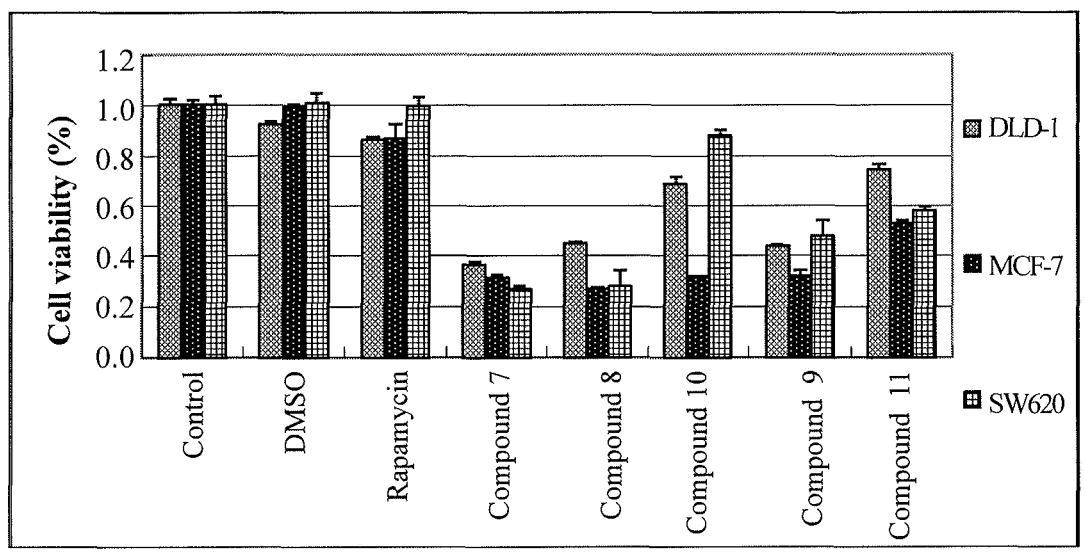
FIG. 1 is a statistical bar graph showing the inhibition activity on the cancer cells of the compounds according to the present invention and Rapamycin.

Unless otherwise stated herein, the terms "a (an)", "the" or the like used in this specification (especially in the Claims hereinafter) shall be understood to encompass both the singular form and the plural form.

The present invention provides a quinoline derivative represented by Chemical Formula (I):

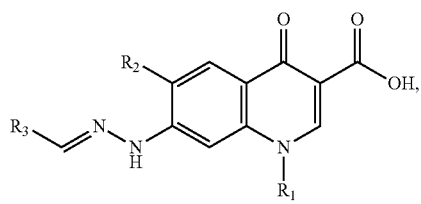
(I)

wherein,
$R_1$ is a substituted or unsubstituted phenyl group;
$R_2$ is a halogen; and
$R_3$ is a substituted or unsubstituted phenyl group, and one of the carbon atoms in the phenyl ring of the phenyl group is optionally substituted by a nitrogen atom (N).

For the quinoline derivative represented by Chemical Formula (I) of the present invention, preferably, $R_1$ is a substituted or unsubstituted

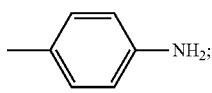

$R_3$ is a substituted or unsubstituted

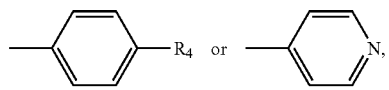

and $R_4$ is a hydrogen, an alkoxy group or a halogen (e.g., —F, —Cl or —Br), wherein the alkoxy group can be, for example, methoxy, ethoxy, propoxy, aryloxy, and so on. $R_2$ is a halogen, i.e., fluorine (F), chlorine (Cl), bromine (Br), iodine (I), or astatine (At). Preferably, $R_2$ is fluorine (F).

In one embodiment of the quinoline derivative of the present invention, $R_1$ is

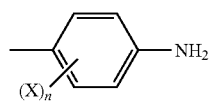

wherein n is an integer ranging from 1 to 4 and X is independently a halogen (e.g., —F, —Cl or —Br), and preferably, $R_1$ is

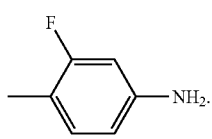

In another embodiment of the quinoline derivative of the present invention, $R_3$ is

The specific embodiments of the quinoline derivative of the present invention include the compounds selected from the group consisting of the following:

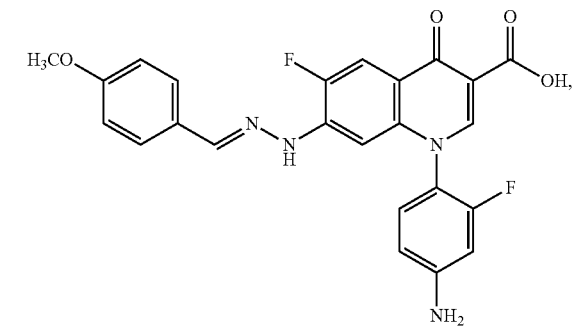

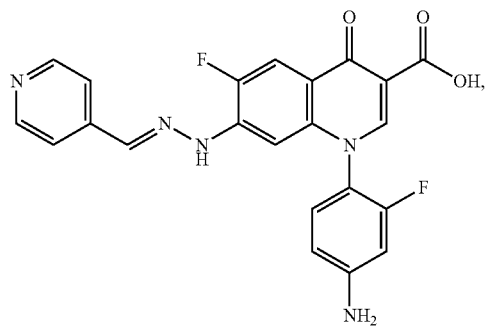

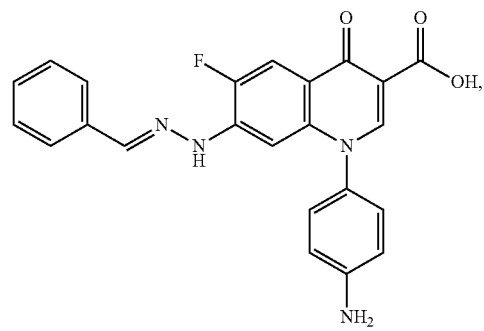

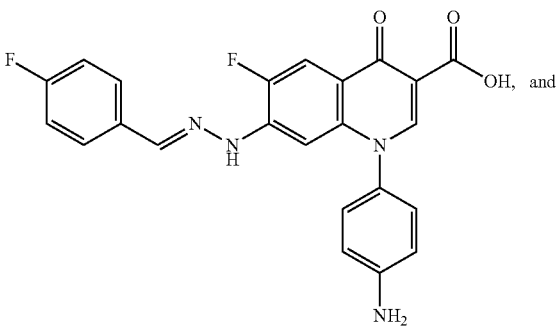
and

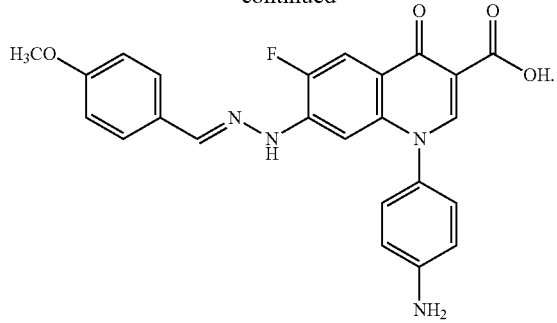

The quinoline derivative of the present invention may be synthesized by using 6,7-difluoro-1-(4-nitrophenyl)-4-oxo-1,4-dihydroquinoline-3-carboxylic acid or 6,7-difluoro-1-(2-fluoro-4-nitrophenyl)-4-oxo-1,4-dihydroquinoline-3-carboxylic acid as starting materials, and then by processes including hydrogenation, hydrazination, and reactions with corresponding arylaldehydes. For example, the starting materials described above may be dissolved in dichloromethane and then hydrogenated using Pd/C as a catalyst under $H_2$ at room temperature and under normal pressure. After the hydrogenation is completed and a purification process is conducted, the purified resultant product is mixed with hydrazine monohydrate dissolved in pyridine, and the mixture is heated to carry out hydrazination. After the hydrazinaction and purification step, the purified resultant product is dissolved in ethanol, and corresponding arylaldehydes are added therein, and the mixture is heated for a period of time. Finally, the quinoline derivative of the present invention is obtained after purification of the resultant product.

The quinoline derivative of the present invention can efficiently inhibit cancer cell proliferation and thus, can be used for treating cancer. As shown in the following examples, the quinoline derivative of the present invention has similar or even superior pharmacological effect to Rapamycin, a clinical anticancer drug, in inhibiting human cancer cell activity. In addition, since the quinoline derivative of the present invention has a smaller molecular weight than Rapamycin, it facilitates the uptake by the body and the translocation to cancer cells, and thus, has potential in the development of new anticancer drugs or targeted drugs.

Therefore, the present invention also provides a pharmaceutical composition, which comprises a pharmaceutically acceptable carrier and an effective amount of the quinoline derivative represented by Chemical Formula (I) or a pharmaceutically acceptable salt or ester thereof. Herein, "an effective amount of the quinoline derivative represented by Chemical Formula (I) or a pharmaceutically acceptable salt or ester thereof" means the total amount of the quinoline derivative of Chemical Formula (I) and a pharmaceutically acceptable salt or ester thereof, which includes one or more provided embodiments of the quinoline derivative of Chemical Formula (I) or a pharmaceutically acceptable salt or ester thereof, can reach the desired therapeutic effect. The quinoline derivative represented by Chemical Formula (I) is as described above.

The quinoline derivative represented by Chemical Formula (I) has at least one dissociable proton (such as the proton on the carboxyl group), which makes the quinoline derivative able to form a pharmaceutically acceptable base addition salt with a suitable organic or inorganic base. Examples of inorganic bases include hydroxides of ammonium, alkali metal, or alkaline earth metal (such as sodium hydroxide, potassium hydroxide, ammonium hydroxide), carbonic acid compounds (such as potassium carbonate), bicarbonate acid compounds and the like. Examples of organic bases include alkoxide, alkanoyl, alkyl and aryl amine, and the like.

The pharmaceutically acceptable ester of the quinoline derivative represented by Chemical Formula (I) means an ester derivative obtained by esterification of a functional group (such as a carboxyl group) on the quinoline derivative of Chemical Formula (I), which can transfer back to the original compound in the body. The above ester derivative includes any physiologically acceptable ester derivative or any ester derivative which can be easily metabolized by the body.

The pharmaceutical composition of the present invention can be used in veterinary and human medicine, and may be in any forms and administrated in any appropriate way. For example, but not limited to, the pharmaceutical composition can be administrated by oral administration, subcutaneous or intravenous injection, etc. A pharmaceutically acceptable carrier may be contained in the pharmaceutical composition of the present invention, depending on the administration form or application of the pharmaceutical composition.

Taking a medicament suitable for the oral administration as an example, pharmaceutically acceptable carriers that will not adversely affect the activity of the quinoline derivative represented by Chemical Formula (I) or a pharmaceutically acceptable salt or ester thereof may be incorporated in the pharmaceutical composition of the present invention, for example, a solvent, an oily solvent, a thinner, a stabilizer, an absorption retarder, a disintegrant, an emulsifier, an antioxidant, a binder, a lubricant, a moisture absorbent, or the like. By using any suitable conventional processes, the composition of the present invention may be formulated into a form suitable for oral administration, for example, into tablets, capsules, granules, pulvis, fluid extracts, solutions, syrups, suspensions, emulsions, tinctures, etc.

When a medicament form suitable for subcutaneous or intravenous injection is desired, one or more additives (such as a pH-adjusting agent, an isotonic agent, a stabilizer, etc.) and solvents (such as an isotonic solution, injection water, a physiological saline solution or a salt buffer solution (e.g., a phosphate buffer solution or a citrate buffer solution)) may be incorporated in the pharmaceutical composition of the present invention to prepare an intravenous fluid injection, an intravenous emulsion injection, a dry powder injection, a suspension injection, a dry powder suspension injection, or the like.

The pharmaceutical composition of the present invention may optionally further comprise additives such as a flavoring agent, a color toner, a coloring agent, and the like to improve the taste and visual experience when the resulting medicament is taken. Also, an appropriate preservative, antiseptic, antimicrobial, antimycotic, or the like may be added to improve the storability of the resulting medicament.

Furthermore, one or more other active components may be optionally incorporated in the pharmaceutical composition of the present invention to further enhance the efficacy of the composition or to increase the flexibility for manufacturing formulations. For example, one or more other anticancer ingredients may be contained in the pharmaceutical composition of the present invention, provided that the other anticancer ingredient (s) will not adversely affect the efficacy of the quinoline derivative represented by Chemical Formula (I) or a pharmaceutically acceptable salt or ester thereof.

Based on the anticancer activity of the quinoline derivative represented by Chemical Formula (I), the pharmaceutical composition of the present invention may be used for treating cancer, such as for treating at least one of colon cancer and breast cancer. Depending on the demand of the subject who receives the administration, the pharmaceutical composition of the present invention may be administrated with different frequencies, such as once every day, several times every day, once every several days, etc.

Mitogen-activated protein kinase (MAPK) pathway is an important cell signal transduction system that induces cell responses. This pathway involves multiple physiological responses, including cell growth, development, division, and death, functional synchronization among cells, and the like. This pathway also plays an important role in the pathological process of malignant transformation of cells (e.g., the generation of cancer cells). Mitogen-activated protein kinases are serine/threonine-specific protein kinases, comprising extracellular signal-regulated kinases (ERK), C-Jun N-terminal kinase (JNK), and p38. Another signal transduction system associated with cell physiological responses and pathological mechanisms is Janus Kinase-Signal Transducer and Activator of Transcription (JAK-STAT) pathway. In this pathway, as the binding of various signals (cellular factors) to a receptor triggers the dimerization of the signal and receptor, Janus Kinase then approaches the dimer and phosphorylates the tyrosine residues on the receptor. The signal transducer and activator of transcription then binds to the receptor, forms into a dimmer, departs from the receptor, and translocates into the cell nucleus, where it binds to a DNA sequence, thereby controlling the expression of a gene.

Without being limited by any theories, it is believed that the pharmaceutical composition of the present invention can inhibit cancer cell through the Janus kinase-signal transducers and activators of the transcription (JAK-STAT) pathway and/or the mitogen-activated protein kinase (MAPK) pathway. Thus, the pharmaceutical composition of the present invention can be used for treating cancers related to at least one of the Janus kinase-signal transducers and activators of transcription (JAK-STAT) pathway or mitogen-activated protein kinase (MAPK) pathway. Specifically, the pharmaceutical composition of the present invention can be used for treating cancers by up-regulating at least one of apoptosis-related cysteine protease 3 (CASP3) gene in the JAK-STAT pathway or growth arrest and DNA damage inducible transcript 3 (GADD153) gene in the MAPK pathway.

The present invention also provides a method for treating cancers in a subject, comprising administrating to the subject an effective amount of the quinoline derivative represented by Chemical Formula (I) or a pharmaceutically acceptable salt or ester thereof. The subject is preferably a mammalian, and more preferably is a human. The quinoline derivative of Chemical Formula (I) is as described above. In one embodiment, the method is for treating at least one of colon cancer and breast cancer. In another embodiment, the method is for treating cancers related to at least one of the Janus kinase-signal transducers and activators of transcription (JAK-STAT) pathway or the mitogen-activated protein kinase (MAPK) pathway. Specifically, the method is for treating cancers by up-regulating at least one of CASP3 gene in the JAK-STAT pathway or GADD153 gene in the MAPK pathway.

Hereinafter, the present invention will be further illustrated with reference to the following examples. However, these examples are only provided for illustration purposes, but not to limit the scope of the present invention.

EXAMPLE

Analysis Methods for Compounds

The melting points of compounds were determined by an Electrothermal IA9100 melting point analysis apparatus (purchased from Clarkson Laboratory, Inc.). The nuclear magnetic resonance (NMR) spectra ($^1$H and $^{13}$C) were measured and recorded by a Varian Gemini 200 spectrometer or Varian-Unity-400 spectrometer (purchased from Varian, Inc). The chemical shifts were expressed in parts per million (δ) with tetramethylsilane (TMS) as an internal standard. Thin-layer chromatography was performed on silica gel 60 F-254 plates (purchased from E. Merck and Co.). The elemental analyses were performed using Heraeus CHN-O Rapid Element Analyzer (purchased from Heraeus Ltd) in the Instrument Center of National Science Council at National Cheng-Kung University and National Chung-Hsing University, Taiwan. All values are within ±0.4% of the theoretical composition.

Preparation Example

The compounds of the present invention were prepared by the method shown in the following Scheme. Hereinafter, the preparation of the compounds will be described in detail.

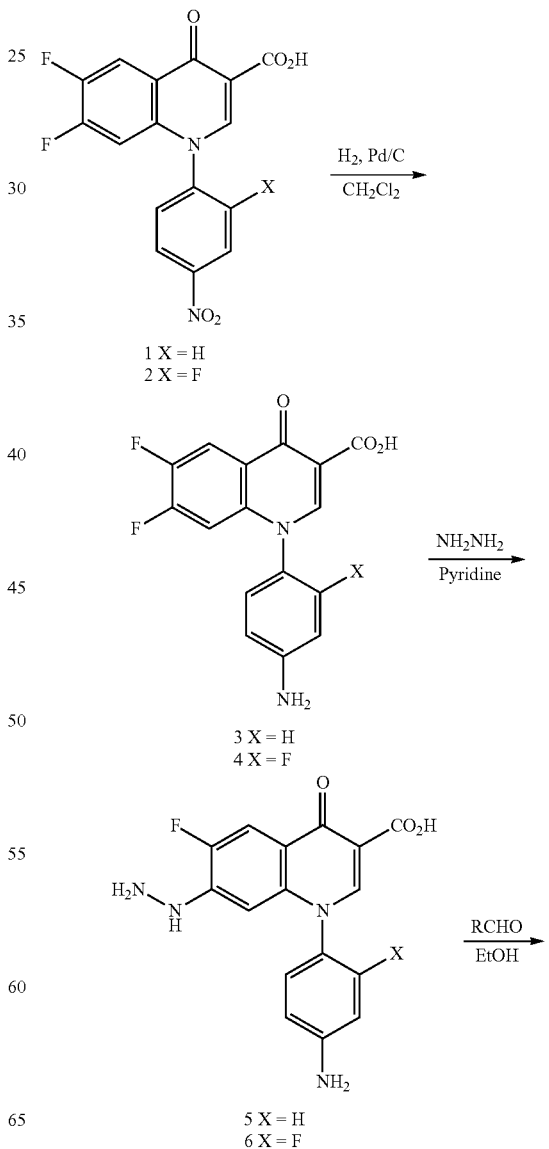

-continued

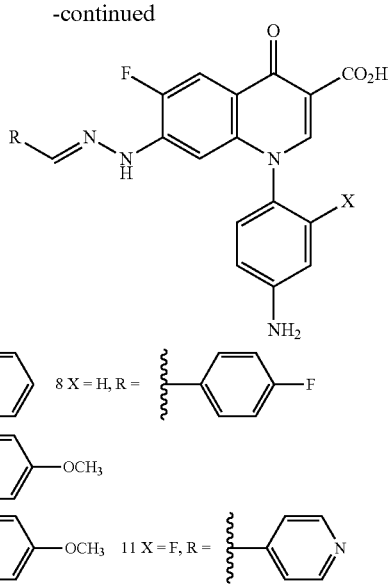

7 X = H, R = phenyl
8 X = H, R = 4-fluorophenyl
9 X = H, R = 4-methoxyphenyl
10 X = F, R = 4-methoxyphenyl
11 X = F, R = 4-pyridyl A. Preparation of 1-(4-aminophenyl)-6,7-difluoro-4-oxo-1,4-dihydroquinoline-3-carboxylic acid (Compound 3) or 1-(4-amino-2-fluorophenyl)-6,7-difluoro-4-oxo-1,4-dihydroquinoline-3-carboxylic acid (Compound 4)

6,7-difluoro-1-(4-nitrophenyl)-4-oxo-1,4-dihydroquinoline-3-carboxylic acid (Compound 1; 0.69 g, 2 mmol) or 6,7-difluoro-1-(2-fluoro-4-nitrophenyl)-4-oxo-1,4-dihydroquinoline-3-carboxylic acid (Compound 2; 0.69 g, 2 mmol) was dissolved in dichloromethane (100 mL)(the preparation method of Compounds 1 and 2 can be seen in Chen et al., J. Med. Chem., 2001, 44, 2374-2377, which is incorporated hereinto by reference), and was hydrogenated for 4 hours (TLC monitoring) under $H_2$ with Pd/C (0.23 g) at room temperature and normal pressure. The reaction mixture was filtered, and the filtrate was concentrated in vacuo to give a residual solid, which was purified by flash column chromatography (FC, silica gel, methanol:dichloromethane=1:50) and recrystallized from ethanol to give 1-(4-aminophenyl)-6,7-difluoro-4-oxo-1,4-dihydroquinoline-3-carboxylic acid (Compound 3, 0.53 g, 84% yield) or 1-(4-amino-2-fluorophenyl)-6,7-difluoro-4-oxo-1,4-dihydroquinoline-3-carboxylic acid (Compound 4, 79% yield).

Compound 3

Melting point: 228-230° C.; $R_f$=0.48 (methanol:dichloromethane=1:20); UV $\lambda_{max}$ nm (log ε): 262 (3.12), 248 (3.04), 241 (2.95), 228 (2.91); IR (KBr): 3341, 1726, 1616, 1493 cm$^{-1}$;
$^1$H-NMR (200 MHz, DMSO-d$_6$) δ 5.72 (br s, NH$_2$), 6.74 (m, 2H, 3',5'-H), 7.19 (dd, 1H, J=6.6, 11.6 Hz, 8-H), 7.27 (m, 2H, 2',6'-H), 8.32 (dd, 1H, J=10.4 Hz, 5-H), 8.62 (s, 1H, 2-H); analysis calculation for $C_{16}H_{10}F_2N_2O_3 \cdot 0.1H_2O$: C, 60.41; H, 3.24; N, 8.81. Found: C, 60.26, H, 3.19, N, 8.43.

Compound 4

Melting point: 224-226° C.; $R_f$=0.42 (methanol:dichloromethane=1:20); UV $\lambda_{max}$ nm (log ε): 258 (3.14), 246 (3.12), 239 (3.01), 230 (2.91); IR (KBr): 3334, 1723, 1614, 1498 cm$^{-1}$;

$^1$H-NMR (200 MHz, DMSO-d$_6$) δ 6.08 (br s, NH$_2$), 6.58 (m, 2H, 3',5'-H), 7.27 (m, 2H, 2',6'-H), 8.33 (dd, 1H, J=8.6, 10.0 Hz, 5-H), 8.76 (s, 1H, 2-H), 14.53 (br s, COOH); analysis calculation for $C_{16}H_9F_3N_2O_3$: C, 59.47; H, 2.71; N, 8.38. Found: C, 57.26; H, 3.02; N, 8.32.

B. Preparation of 1-(4-aminophenyl)-6-fluoro-7-hydrazinyl-4-oxo-1,4-dihydroquinoline-3-carboxylic acid (Compound 5) or 1-(4-amino-2-fluorophenyl)-6-fluoro-7-hydrazinyl-4-oxo-1,4-dihydroquinoline-3-carboxylic acid (Compound 6)

Either Compound 3 (0.89 g, 2.81 mmol) or Compound 4 (0.94 g, 2.84 mmol) was mixed with hydrazine monohydrate (2.2 mL, 45 mmol) in pyridine (8 mL) to obtain a mixture, and then, the mixture was heated at 70-80° C. for 6 hours (TLC monitoring). The reactant was cooled and acetic acid was added thereinto until a pH of 5, and then the precipitate was collected by filtration, washed with $H_2O$, and recrystallized from ethanol to give 1-(4-aminophenyl)-6-fluoro-7-hydrazinyl-4-oxo-1,4-dihydroquinoline-3-carboxylic acid (Compound 5, 0.67 g, 73% yield) as a yellow solid or 1-(4-amino-2-fluorophenyl)-6-fluoro-7-hydrazinyl-4-oxo-1,4-dihydroquinoline-3-carboxylic acid (Compound 6, 76% yield).

Compound 5

Melting point: 258-260° C.; $R_f$=0.42 (methanol:dichloromethane=1:20); UV $\lambda_{max}$ nm (log ε): 282 (3.07), 258 (2.92), 254 (2.77), 232 (2.73); IR (KBr) 3326, 1713, 1624, 1466 cm$^{-1}$;
$^1$H-NMR (200 MHz, DMSO-d$_6$) δ 4.31 (br s, hydrazine-NH$_2$), 5.64 (br s, 4'-NH$_2$), 6.75 (m, 3H, 3',5', 8-H), 7.21 (m, 2H, 2',6'-H), 7.78 (d, 1H, J=12.2 Hz, 5-H), 8.21 (br s, 7-NH), 8.38 (s, 1H, 2-H), 15.70 (br s, 1H, COOH); analysis calculation for $C_{16}H_{13}FN_4O_3 \cdot 0.2H_2O$: C, 57.89, H, 4.08, N, 16.88. Found: C, 57.98; H, 4.19; N, 16.58.

Compound 6

Melting point: 283-285° C.; $R_f$=0.39 (methanol:dichloromethane=1:20); UV $\lambda_{max}$ nm (log ε): 286 (3.12), 278 (3.07), 252 (2.85), 238 (2.76); IR (KBr): 3350, 1705, 1629, 1464 cm$^{-1}$;
$^1$H-NMR (200 MHz, DMSO-d$_6$) δ 4.35 (br s, hydrazine-NH$_2$), 5.99 (br s, 4'-NH$_2$), 6.52-6.61 (m, 2H, 3',5'-H), 6.71 (d, 2H, J=6.2 Hz, 8-H), 7.327-7.36 (m, 2H, 2',6'-H), 7.78 (d, 1H, J=12.4 Hz, 5-H), 8.28 (br s, 7-NH), 8.47 (s, 1H, 2-H), 15.38 (br s, 1H, COOH); analysis calculation for $C_{16}H_{12}F_2N_4O_3 \cdot 0.2H_2O$: C, 54.09; H, 3.69; N, 15.77. Found: C, 54.07, H, 3.75, N, 15.69.

C. Preparation of Compounds 7 to 11 of the present invention 7-(2-Arylidenehydrazinyl)fluoroquinolone carboxylic acid derivatives Either Compound 5 or Compound 6 (2 mmol) was dissolved in ethanol (30 mL), and then, an appropriate arylaldehyde (4 mmol) with the aldehyde structure shown in the above scheme was added thereinto. Then, the mixture was heated and refluxed for 8 to 48 hours (TLC monitoring). The solvent was removed in vacuo, and the residue was suspended in $H_2O$ (20 mL). The resulting precipitate was purified by FC (methanol:dichloromethane=1:50) and recrystallized from ethanol to give the final products of Compounds 7 to 11 (i.e., 7-(2- arylidenehydrazinyl)fluoroquinolone carboxylic acid derivatives). The details of Compounds 7 to 11 of the present invention are as follows.

Compound 7

1-(4-aminophenyl)-7-(2-benzylidenehydrazinyl)-6-fluoro-4-oxo-1,4-dihydroquinoline-3-carboxylic acid

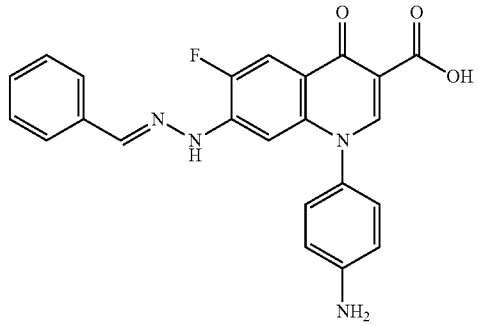 [SMILES: Nc1ccc(-n2cc(C(=O)O)c(=O)c3cc(F)c(N/N=C/c4ccccc4)cc32)cc1]

Yellow solid (88% yield); melting point: 314-316° C.; $R_f$=0.46 (methanol:dichloromethane=1:10); UV $\lambda_{max}$ nm (log ϵ): 378 (3.34), 358 (3.27), 310 (3.39), 296 (3.32), 272 (3.24), 242 (3.33); IR (KBr): 3381, 1708, 1628, 1462 cm$^{-1}$; $^1$H-NMR (200 MHz, DMSO-d$_6$) δ: 5.77 (br s, NH$_2$), 6.80-6.82 (m, 2H, 3',5'-H), 7.15 (d, 1H, J=7.2 Hz, 8-H), 7.27-7.48 (m, 7H, 2',6', Ar—H), 7.95 (d, 1H, J=11.6 Hz, 5-H), 8.18 (s, 1H, HC=N), 8.54 (s, 1H, 2-H), 11.22 (br s, NH), 15.47 (br s, COOH); analysis calculation for C$_{23}$H$_{17}$FN$_4$O$_3$.0.3H$_2$O: C, 65.49; H, 4.20; N, 13.28. Found: C, 65.38; H, 4.35; N, 13.11.

Compound 8

1-(4-aminophenyl)-6-fluoro-7-[2-(4-fluorobenzylidene)hydrazinyl]-4-oxo-1,4-dihydroquinoline-3-carboxylic acid

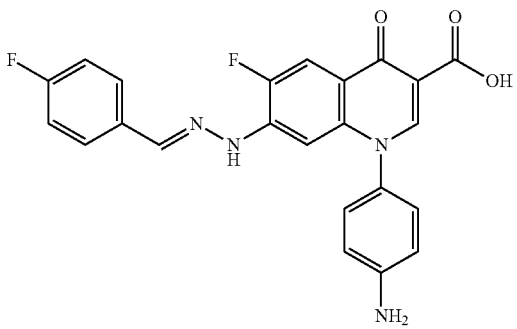 [SMILES: Nc1ccc(-n2cc(C(=O)O)c(=O)c3cc(F)c(N/N=C/c4ccc(F)cc4)cc32)cc1]

Yellow solid (85% yield); melting point: 308-310° C.; $R_f$=0.50 (methanol:dichloromethane=1:10); UV $\lambda_{max}$ nm (log ϵ): 374 (3.28), 312 (3.32), 298 (3.30), 286 (3.26), 254 (3.22), 234 (3.24); IR (KBr): 3214, 1633, 1505, 1470 cm$^{-1}$; $^1$H-NMR (200 MHz, DMSO-d$_6$) δ 5.72 (br s, NH$_2$), 6.78-6.80 (m, 2H, 3',5'-H), 7.03 (d, 2H, J=6.4 Hz, 8-H), 7.14-7.24 (m, 4H, 2',6'-H, Ar—H), 7.46-7.49 (m, 2H, Ar—H), 7.75 (d, 1H, J=11.2 Hz, 5-H), 8.13 (s, 1H, HC=N), 8.54 (s, 1H, 2-H), 11.03 (br s, NH), 15.42 (br s, COOH); analysis calculation for C$_{23}$H$_{16}$F$_2$N$_4$O$_3$: C, 63.59; H, 3.71; N, 12.90. Found: C, 63.31; H, 3.99; N, 12.81.

Compound 9

1-(4-aminophenyl)-6-fluoro-7-(2-(4-methoxybenzylidene)hydrazinyl)-4-oxo-1,4-dihydroquinoline-3-carboxylic acid

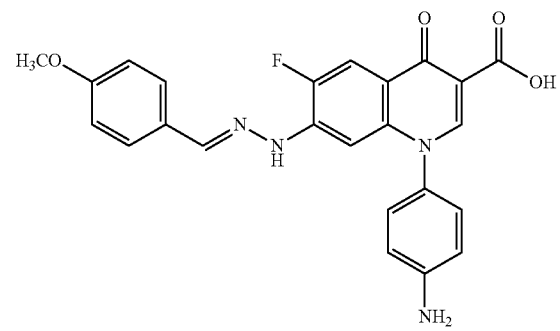 [SMILES: COc1ccc(/C=N/Nc2cc3c(cc2F)c(=O)c(C(=O)O)cn3-c2ccc(N)cc2)cc1]

Yellow solid (85% yield); melting point: 307-309° C.; $R_f$=0.45 (methanol:dichloromethane=1:10); UV $\lambda_{max}$ nm (log ϵ): 380 (2.82), 328 (2.90), 310 (2.96), 294 (2.84), 252 (2.75), 232 (2.72); IR (KBr): 3247, 1702, 1626, 1465 cm$^{-1}$; $^1$H-NMR (200 MHz, DMSO-d$_6$) δ 3.81 (s, 3H, OCH$_3$), 5.78 (br s, NH$_2$), 6.79-6.83 (m, 2H, 3',5'-H), 6.97-7.01 (m, 2H, Ar—H), 7.12 (d, 1H, J=6.2 Hz, 8-H), 7.25-7.30 (m, 2H, 2',6'-H), 7.39-7.44 (m, 2H, Ar—H), 7.93 (d, 1H, J=12.0 Hz, 5-H), 8.14 (s, 1H, HC=N), 8.54 (s, 1H, 2-H), 11.08 (br s, NH) 15.39 (br s, COOH); analysis calculation for C$_{24}$H$_{19}$FN$_4$O$_4$.0.2H$_2$O: C, 64.05; H, 4.34; N, 12.45. Found: C, 63.96; H, 4.42; N, 12.31.

Compound 10

1-(4-amino-2-fluorophenyl)-6-fluoro-7-[2-(4-methoxybenzylidene)hydrazinyl]-4-oxo-1,4-dihydroquinoline-3-carboxylic acid

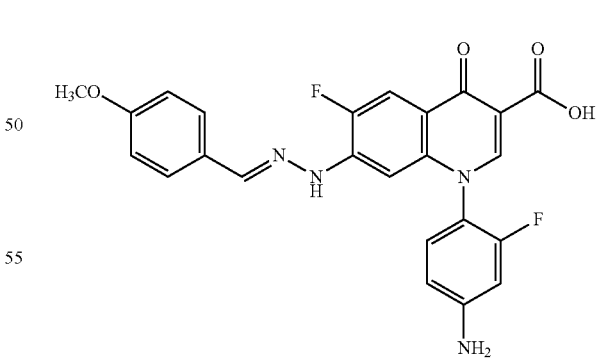

Yellow solid (86% yield); melting point: 321-322° C.; $R_f$=0.48 (methanol:dichloromethane=1:10); UV $\lambda_{max}$ nm (log ϵ): 376 (3.32), 332 (3.16), 318 (3.31), 305 (3.38), 252 (3.34), 228 (3.22); IR (KBr): 3363, 1796, 1627, 1461 cm$^{-1}$; $^1$H-NMR (200 MHz, DMSO-d$_6$) δ: 3.80 (s, 3H, OCH$_3$), 6.16 (br s, 2H, NH$_2$), 6.63-6.65 (m, 2H, 3',5'-H), 6.98-7.01 (m, 3H, 8-, Ar—H), 7.37-7.43 (m, 3H, 6'-, Ar—H), 7.94 (d, 2H, J=11.6 Hz, 5-H), 8.14 (s, 1H, HC=N), 8.66 (s, 1H, 2-H), 11.15 (br s, NH), 15.35 (br s, COOH; analysis calculation for $C_{24}H_{18}F_2N_4O_4 \cdot 0.2H_2O$: C, 61.59; H, 3.96; N, 11.97. Found: C, 61.60, H, 4.27, N, 11.81.

Compound 11

1-(4-amino-2-fluorophenyl)-6-fluoro-4-oxo-7-[2-(pyridin-4-ylmethylene)hydrazinyl]-1,4-dihydro-quinoline-3-carboxylic acid

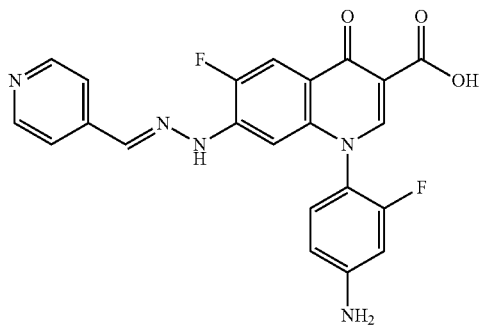 [SMILES: Nc1ccc(-n2cc(C(=O)O)c(=O)c3cc(F)c(N/N=C/c4ccncc4)cc32)c(F)c1]

Yellow solid (71% yield); melting point: 176-178° C.; $R_f$=0.43 (methanol:dichloromethane=1:10); UV $\lambda_{max}$ nm (log $\epsilon$): 374 (3.37), 367 (3.34), 3.16 (3.41), 302 (3.45), 281 (3.58), 256 (3.55), 238 (3.47); IR (KBr): 3356, 1721, 1631, 1467 cm$^{-1}$; $^1$H-NMR (200 MHz, DMSO-d$_6$) δ: 6.18 (br s, NH$_2$), 6.66-6.72 (m, 2H, 3',5'-H), 7.06 (dd, 1H, J=6.8, 1.2 Hz, 8-H), 7.34-7.50 (m, 2H, 6'-, pyridinyl-H), 7.64-7.67 (m, 2H, pyridinyl-H), 7.95 (d, 1H, J=12.0 Hz, 5-H), 8.09 (s, 1H, HC=N), 8.41 (s, 1H, 2-H), 8.59-8.64 (m, 1H, pyridinyl-H), 11.49 (br s, NH), 15.26 (br s, COOH; analysis calculation for $C_{22}H_{15}F_2N_5O_3 \cdot 1.0H_2O$: C, 58.28; H, 3.78; N, 15.45. Found: C, 58.19; H, 4.03; N, 15.40.

[Compound Activity Test 1]

The inhibition activity on cancer cells of the above prepared Compounds 7 to 11 of the present invention was tested by using MTT (3-[4,5-dimethylthiazol-2-yl]-2,5-diphenyltetrazolium bromide) assay.

Human colon cancer cells DLD-1 (BCRC: 60132) and SW620 (BCRC: 60343), and human breast cancer cell MCF-7 (BCRC: 60436) (The cell lines were purchased from Bioresource Collection and Research Center (BCRC), Taiwan) were cultured with Dulbecco's modified eagle's medium (DMEM medium) in an incubator at 37° C. under 5% CO$_2$, respectively. After 2 to 3 days, the growth of each cancer cell line was observed, and the cytotoxicity test was performed when the cells grew to a confluence state.

10$^5$ cells/well were seeded in a 24-well plate, and cultured for 12 to 16 hours. Then, Compounds 7 to 11 (1 μM) of the present invention, Rapamycin (a conventional anticancer drug as a comparative group, 1 μM), or dimethyl sulfoxide (DMSO, as a control group) was added into the medium. After 24-hour treatment, the morphological change of the cells was observed by an inverted microscope, and cell viability was determined by the MTT assay.

The MTT assay is commonly used to determine cytotoxicity. MTT, a yellow water-soluble compound, can be reduced by dehydrogenase in the mitochondria of cells to yield an insoluble purple product (3-[4,5-dimethylthiazol-2-yl]-2,5-diphenyl-formazan), which is then precipitated and accumulated in the cells. Dimethyl sulfoxide can be added to dissolve (3-[4,5-dimethylthiazol-2-yl]-2,5-diphenyl-formazan), and then the absorbance at a wavelength of 589 nm can be measured. Herein, active dehydrogenase only exists in living cells, and therefore, the absorbance is proportional to the number of living cells, and cell viability may be evaluated accordingly.

The results of the above experiment are shown in FIG. 1. As shown in FIG. 1, Compounds 7 to 11 of the present invention have excellent effects in inhibiting human cancer cells, and thus, can be used for treating cancer. In addition, Compounds 7 to 11 of the present invention have superior anticancer activity to Rapamycin, and also have smaller molecular weights than Rapamycin, which facilitates uptake by the body and the translocation to cancer cell, and thus, these compounds can effectively treat cancer.

[Compound Activity Test 2]

The same procedure as the above compound activity test 1 was performed except that Rapamycin, a clinical anticancer drug, was used as a comparative group, and human breast cancer cell MCF-7 was used to carry out the assay to observe the inhibiting activity on cancer cell of the compounds of the present invention at different time points. Results are shown in FIG. 2.

Figure 2:
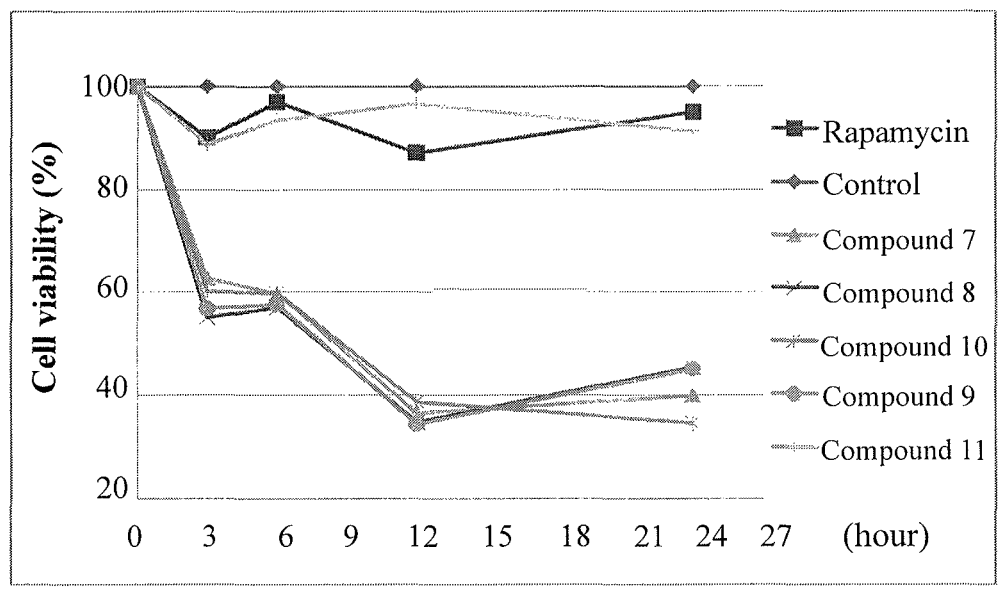
FIG. 2 is a curve graph showing the inhibition activity on the cancer cells of the compounds according to the present invention and Rapamycin.

As shown in FIG. 2, Compounds 7 to 11 of the present invention have similar or even superior anticancer activity to Rapamycin, and thus, these compounds can effectively treat cancer.

[Compound Anticancer Mechanism Test 1]

DNA microarray and bioinformatics tools were used to analyze the mechanism of action of Compounds 7 to 11 of the present invention. First, 10$^7$ of human breast cancer cell MCF-7 were seeded in each plate, and cultured for 12 hours. Then, Compounds 7 to 11 (the experimental groups) of the present invention and dimethyl sulfoxide (the control group) were added into the plate, respectively. After 6 hours, a TRIzol reagent (purchased from Invitrogen, Inc) was used for isolating total RNA of the cells, while RNA purity (260/280) above 1.8 was confirmed.

The isolated mRNA was reversely transcribed into cDNA, then, treated with green fluorescent dye Cyanine 3 (Cy3). Equal amounts of cDNA of the experimental group and the control group were taken and were hybridized with the cDNA on a biochip (microarray, Agilent Human G3 Whole Genome Oligo 8x60K Biochip) according to base pairing rules.

Figure 3:
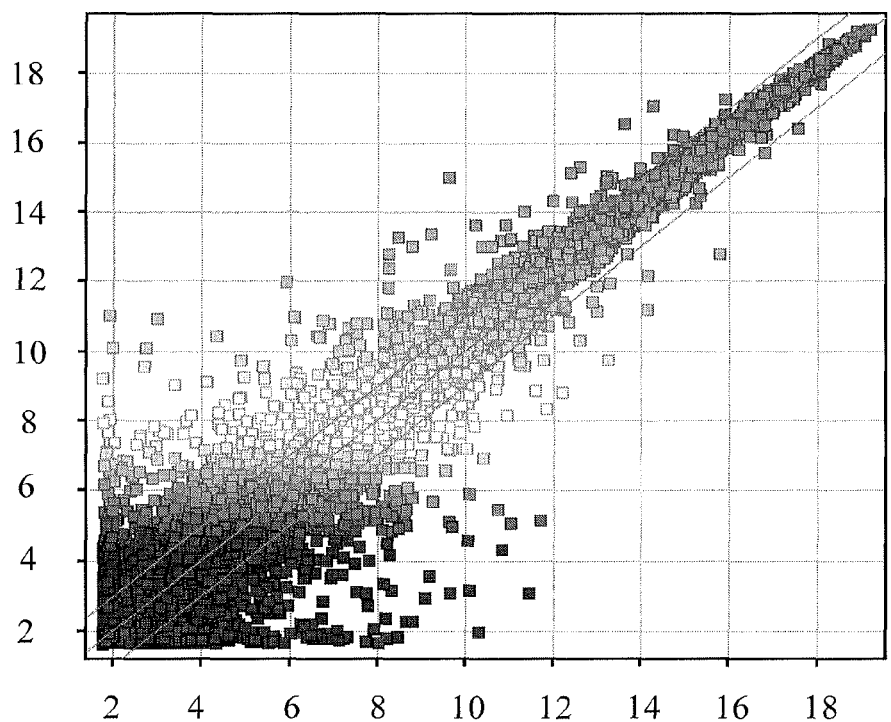
FIG. 3 is a graph of DNA microarray analysis for dissecting the mechanism of action of the compounds according to the present invention.
Figure 4:
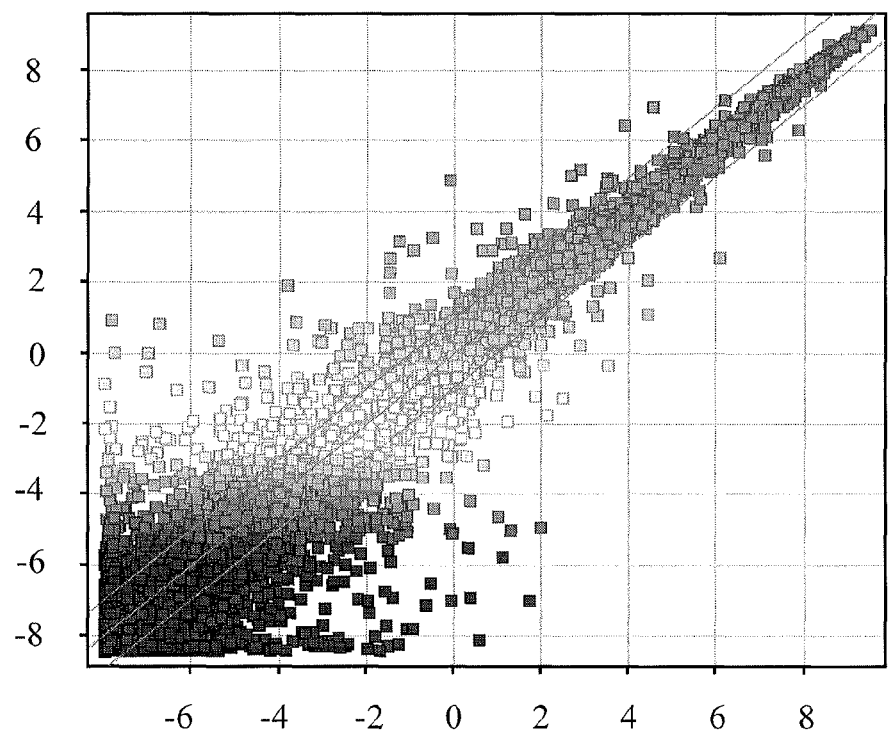
FIG. 4 is a graph of DNA microarray analysis for dissecting the mechanism of action of the compounds according to the present invention.

Finally, the laser scanning image analysis and data were normalized. Significantly up-regulated and down-regulated genes in the experiment were selected under the standard fold change of 2, and the pathway of the selected genes was further analyzed through bioinformatics websites: DAVID (DAVID Functional Annotation Bioinformatics Microarray Analysis) and KEGG (Kyoto Encyclopedia of Genes and Genomes). The normalized microarray data is shown in FIGS. 3 and 4. The analysis results of the bioinformatics tools are tabulated in Table 1.

TABLE 1

| Type | count | % | p value |
|---|---|---|---|
| aminoacyl-tRNA biosynthesis | 6 | 1.3 | 0.0014 |
| JAK-STAT signal transduction pathway | 10 | 2.1 | 0.0044 |
| cytokine-cytokine receptor interaction | 13 | 2.7 | 0.0073 |
| p53 signal transduction pathway | 5 | 1.1 | 0.051 |
| MAPK signal transduction pathway | 10 | 2.1 | 0.099 |
| vitamin A metabolism | 4 | 0.8 | 0.1 |

The analysis results of the DNA microarray and bioinformatics tools shown in FIG. 3, FIG. 4, and Table 1 showed that after the samples were treated with the compounds of the present invention, the genes with remarkably different expression relate to the Janus kinase-signal transducers and activators of transcription (JAK-STAT) pathway and/or the mitogen-activated protein kinase (MAPK) pathway. The results indicated that the mechanism of anticancer action of the compounds of the present invention involves the Janus kinase-signal transducers and activators of transcription pathway and/or the mitogen-activated protein kinase pathway.

[Compound Anticancer Mechanism Test 2]

Apoptosis-related cysteine protease 3 (CASP3) gene and growth arrest and DNA damage inducible transcript 3 (GADD153) gene are essential genes for cell apoptosis, and the increase in the expression of these genes may lead to cell apoptosis. The two genes selected were shown to be up-regulated by the compounds of the present invention in the DNA microarray experiments, indicating that the compounds of the present invention can promote cell apoptosis. To further confirm that the anticancer effect of the compounds of the present invention was via the JAK-STAT and MAPK pathways, human breast cancer cell MCF-7 was used to study the CASP3 gene expression in the JAK-STAT pathway and GADD153 gene expression in the MAPK pathway by performing reverse transcription polymerase chain reaction (RT-PCR).

MCF-7 cells with or without treatment of the compounds of the present invention were grown to 80% confluence. The total amount of RNA from the cells was isolated by the TRIzol reagent (purchased from Invitrogen, Inc). For each sample, 5 μg of total RNA was reversely transcribed into first strand cDNA using a SuperscriptII kit (purchased from Invitrogen, Inc) with oligo-dT primers, according to the manufacturer's protocol. The PCR was conducted under the following conditions on an Applied biosystems 2720 Thermal Cycler machine: (1) heating: 94° C. (2 minutes), and 30 cycles of (2) 94° C. (denaturation, 30 seconds), 55° C. (annealing, 1 minute), and 72° C. (elongation, 1 minute). The following primers were used:

(a) growth arrest and DNA damage inducible transcript 3 (GADD153) gene:

```
Sense:
                                         (SEQ ID NO: 1)
5'-GGG AAG TAG AGG CGA CTC G-3'

Antisense:
                                         (SEQ ID NO: 2)
5'-CTT CCC CCT GCG TAT GTG-3'
```

(b) apoptosis-related cysteine protease 3 (CASP3) gene:

```
Sense:
                                         (SEQ ID NO: 3)
5'-AGA ACT GGA CTG TGG CAT TGA G-3'

Antisense:
                                         (SEQ ID NO: 4)
5'-GCT TGT CGG CAT ACT GTT TCA G-3'
```

(c) actin primers (as an internal control group) gene:

```
Sense:
                                         (SEQ ID NO: 5)
5'-GCT CGT CGT CGA CAA CGG CTC-3'

Antisense:
                                         (SEQ ID NO: 6)
5'-CAA ACA TGA TCT GGG TCA TCT TCT C-3'
```

Figure 5:
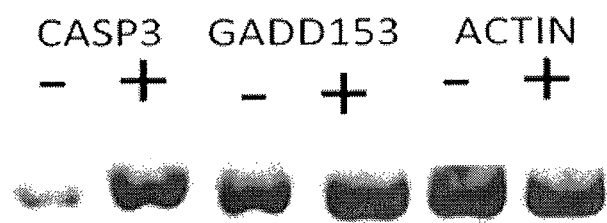
FIG. 5 is a cDNA electrophoretogram of CASP3 gene and GADD153 gene.

All PCR products were then analyzed in 1 wt/vol % agarose TBE gel (purchased from Invitrogen, Inc) by electrophoresis. The results are shown in FIG. 5. As shown in FIG. 5, the expression of CASP3 gene and GADD153 gene in the MCF-7 cancer cells treated with the compounds of the present invention increased, verifying that the anticancer effect of the compounds of the present invention is achieved via the JAK-STAT pathway and MAPK pathway.

As a result, the above examples indicate that the compounds of the present invention can be used for treating cancers related to the JAK-STAT pathway and/or the MAPK pathway.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

---

What is claimed is:

1. A quinoline derivative represented by Chemical Formula (I):

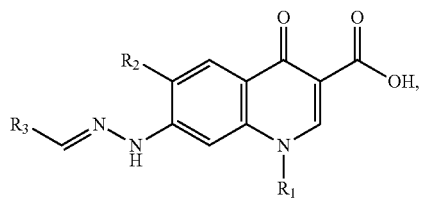

(I)

wherein, $R_1$ is a substituted or unsubstituted phenyl group;

$R_2$ is a halogen; and $R_3$ is a substituted or unsubstituted phenyl group, and one of the carbon atoms in the phenyl ring of the phenyl group is optionally substituted by a nitrogen atom (N).

2. The quinoline derivative as claimed in claim 1, wherein $R_1$ is an unsubstituted

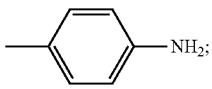

$R_3$ is an unsubstituted

and $R_4$ is a hydrogen.

3. The quinoline derivative as claimed in claim 2, wherein $R_1$ is

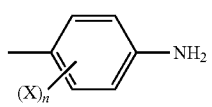

wherein n is an integer ranging from 1 to 4 and X is independently a halogen.

4. The quinoline derivative as claimed in claim 3, wherein $R_1$ is

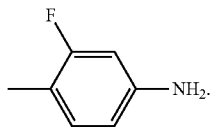

5. The quinoline derivative as claimed in claim 2, wherein $R_3$ is

6. The quinoline derivative as claimed in claim 1, which is selected from the group consisting of:

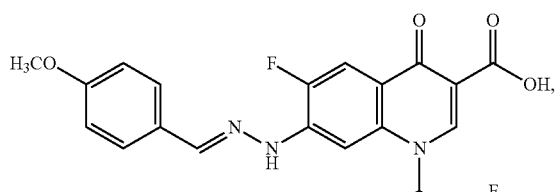

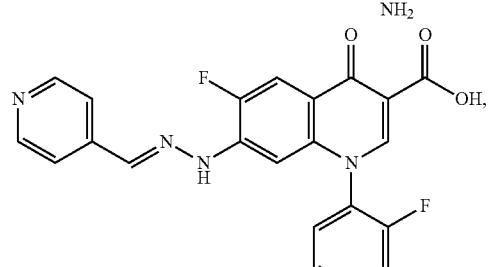

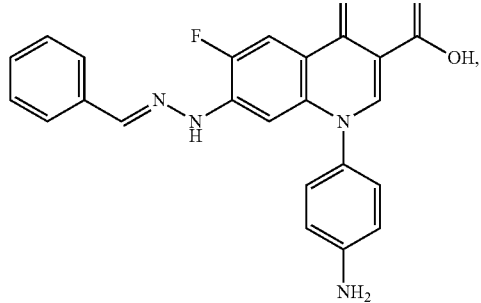

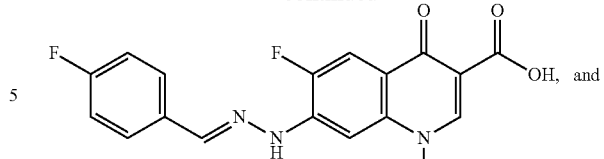

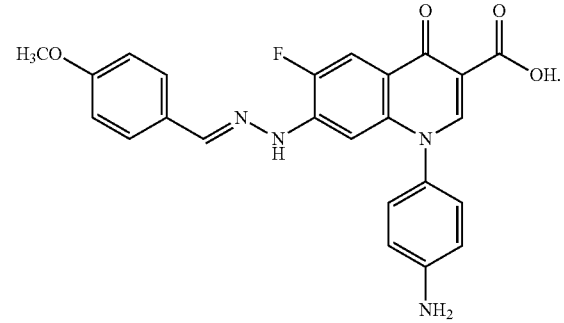

7. A pharmaceutical composition for up-regulating at least one of the Janus kinase-signal transducers and activators of transcription (JAK-STAT) pathway or mitogen-activated protein kinase (MAPK) pathway, comprising a pharmaceutically acceptable carrier and an effective amount of the quinoline derivative as claimed in claim 1 or a pharmaceutically acceptable salt or ester thereof.

8. The pharmaceutical composition as claimed in claim 7, which is for treating cancers by up-regulating at least one of apoptosis-related cysteine protease 3 (CASP3) gene in the JAK-STAT pathway or growth arrest and DNA damage inducible transcript 3 (GADD153) gene in the MAPK pathway.

9. A method for up-regulating at least one of the Janus kinase-signal transducers and activators of transcription (JAK-STAT) pathway or mitogen-activated protein kinase (MAPK) pathway, comprising administrating to the subject an effective amount of the quinoline derivative as claimed in claim 1 or a pharmaceutically acceptable salt or ester thereof.

10. The method as claimed in claim 9, which is for up regulating at least one of CASP3 gene in the JAK-STAT pathway or GADD153 gene in the MAPK pathway.

11. The method as claimed in claim 10, wherein the subject is a mammalian.

12. The method as claimed in claim 11, wherein the mammalian is a human.

* * * * *